United States Patent [19]

Suzuki

[11] 4,153,809

[45] May 8, 1979

[54] EXTRACTIVE SEPARATION OF GLYCOLIC ACID FROM DIGLYCOLIC ACID

[75] Inventor: Shigeto Suzuki, San Francisco, Calif.

[73] Assignee: Chevron Research Company, San Francisco, Calif.

[21] Appl. No.: 823,577

[22] Filed: Aug. 11, 1977

[51] Int. Cl.$^2$ ...................... C07C 59/23; C07C 59/06
[52] U.S. Cl. ..................................... 562/583; 562/579
[58] Field of Search ........................ 260/535 P, 535 R; 562/579, 583

[56] References Cited

U.S. PATENT DOCUMENTS 3,997,599  12/1976  Grinstead .................... 260/535 P Primary Examiner—Paul J. Killos
Attorney, Agent, or Firm—D. A. Newell; John Stoner, Jr.; A. T. Bertolli

[57] ABSTRACT

Diglycolic acid is separated from glycolic acid by preferential extraction from an aqueous mixture of the two acids using an organic solution of a water-insoluble trihydrocarbylphosphine oxide as the extraction agent.

10 Claims, No Drawings

EXTRACTIVE SEPARATION OF GLYCOLIC ACID FROM DIGLYCOLIC ACID

BACKGROUND OF THE INVENTION

This invention concerns the extractive separation of diglycolic acid from glycolic acid. In particular, diglycolic acid is extracted from aqueous mixtures of glycolic acid and diglycolic acid using an organic solution of a water-insoluble trihydrocarbylphosphine oxide.

U.S. Pat. No. 3,911,003, granted Oct. 7, 1975, describes the hydrogen fluoride-catalyzed reaction of aqueous formaldehyde and carbon monoxide to give glycolic acid. As described at Col. 3, the product is an aqueous mixture of glycolic acid and diglycolic acid. While the concentration of diglycolic acid can be minimized by maintaining a formaldehyde to water reactant ratio below about 4:1, some diglycolic acid is always produced. Fortunately, both acids are items of commerce, which when separated are readily marketable.

Unfortunately, glycolic acid and diglycolic acid are highly polar acids and, therefore, difficult to separate by either crystallization or distillation. As a consequence, where the acids are intended for use in the production of glycols, they are usually separated by esterifying the acids and hydrogenating the esters to form ethylene glycol and diethylene glycol, which can be separated by distillation. Where the acids themselves are desired, they are separated by distilling the esters, which can subsequently be hydrolyzed back to the acids. The major drawback to these separation procedures is the need to convert the acids to their corresponding esters prior to separation. It would be considerably more efficient to separate the acids as such.

Solvent extraction is one method of separation which has been used to separate highly polar organic compounds as such. Suitable extractants must have a preferential high solvent power for the component to be extracted. Thus, in the case of an aqueous mixture of glycolic acid and diglycolic acid, a suitable extractant must preferentially extract one or the other of the acids. The effectiveness of a two-phase extraction procedure depends upon the solvent power of the extractant and is measured by beta values. The beta value of a two-component extraction is defined by the expression:

$$\beta_{BA} = \frac{\text{(Weight of component A in aqueous phase)}}{\text{(Weight of component A in organic phase)}} \div \frac{\text{(Weight of Component B in aqueous phase)}}{\text{(Weight of Component B in organic phase)}}$$

In general, a beta value of at least 2 is required for an economical extraction process.

Accordingly, it would be advantageous to separate aqueous mixtures of diglycolic acid and glycolic acid using solvent extraction carried out with an extractant which provides a beta value in excess of 2 under typical operating conditions.

SUMMARY OF THE INVENTION

It has been found that organic solutions of trihydrocarbylphosphine oxides can be used to preferentially extract diglycolic acid from aqueous mixtures with glycolic acid. Thus, this invention provides a process for separating diglycolic acid from aqueous mixtures with glycolic acid by: (1) contacting the aqueous mixture with a non-miscible organic solution of a water-insoluble trihydrocarbylphosphine oxide to form a two-phase system having an organic phase rich in diglycolic acid and an aqueous phase rich in glycolic acid; and (2) separating the organic phase from the aqueous phase.

DETAILED DESCRIPTION OF THE INVENTION

The extraction process produced by this invention is based, among other factors, on the discovery that certain water inmiscible organic solutions preferentially extract diglycolic acid from aqueous mixtures with glycolic acid. The phases of the resulting two-phase system can be readily separated. The organic solutions suitable for use in this process comprises a trihydrocarbylphosphine oxide dissolved in a water insoluble solvent. In general, trihydrocarbylphosphine oxides which possess the characteristics of a suitable diglycolic acid acid extractant have the formula

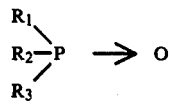

wherein $R_1$, $R_2$, and $R_3$ are independently branched or straight chain alkyl groups containing from about 1 to about 30, preferably from about 1 to about 16, carbon atoms provided that the total number of carbon atoms in $R_1$, $R_2$ and $R_3$ is at least 12, preferably 15; aryl, alkaryl or aralkyl groups containing from 6 to 30, preferably from 6 to about 20 carbon atoms, provided that the total number of carbon atoms in $R_1$, $R_2$ and $R_3$ is at least 14, preferably 17; or cycloalkyl groups of 5 to 30, preferably 5 to 20 carbon atoms, provided that the total number of carbon atoms in $R_1$, $R_2$ and $R_3$ is at least 12, preferably 15. They can be prepared by the oxidation of the corresponding trihydrocarbylphosphine which can, in turn, be prepared by the reaction of Grignard reagents or alkyllithiums with phosphorus trichloride. These compounds have all the characteristics of an efficient extractant. They have a preferential high solvent power for diglycolic acid, particularly diglycolic acid in aqueous solution with glycolic acid. At the same time, the trihydrocarbylphosphine oxides are water-insoluble. Thus, losses of the extractants during contact with the aqueous mixture are minimal.

Specific suitable trihydrocarbylphosphine oxides include, for example: tri-n-octylphosphine oxide, tridecylphosphine oxide, n-hexadecyldimethylphosphine oxide, octacosyldiethylphosphine oxide, eicosylpropylbutylphosphine oxide, 2-ethylheptyloctylmethylphosphine oxide, 3-methyldodecyldimethylphosphine oxide, tri-(2-ethylhexyl)phosphine oxide, triphenylphosphine oxide, diphenyloctylphosphine oxide, naphthyldihexylphosphine oxide, tritolylphosphine oxide, hexylphenyldibutylphosphine oxide, cumylphenyloctadecylphosphine oxide, dodecylphenyldimethylphosphine oxide, 2-phenylethyldiheptylphosphine oxide, 3-(4-tolyl)hexyldiethylphosphine oxide, tri-(2-phenylpropyl)phosphine oxide, tricyclohexylphosphine oxide, cyclooctyldioctylphosphine oxide, cyclododecyldiethylphosphine oxide, 3-ethylcyclohexyldibutylphosphine oxide, 2-cyclopentyldodecyldipropylphosphine oxide, cyclohexylphenyloctylphosphine oxide. Tri-n-octylphosphine oxide has been found particularly effective.

The trihydrocarbylphosphine oxides described above are used in organic solution with a suitable solvent to form an extractant. For example, from about 5% to about 90%, preferably 20% to 70%, by weight of the phosphine oxide can be dissolved in a water insoluble organic liquid solvent. Suitable solvents include, for example: aromatic compounds such as benzene, toluene, xylenes, mesitylene, cumene, methylnaphthalene, dichlorobenzene, dodecylbenzene, diphenylether, anisole, propylphenyl ether, 4-nitrobutylbenzene, bromobenzene; and aliphatic compounds such as n-octane, 3-methyldecane, 2-dodecane, hexylcyclohexane, di-2-ethylhexyl ether, 4-chlorononane, tetrachloromethylene, and the like. The particular solvent which is used to carry the trialkylphosphine oxide can vary widely; however, benzene has been found to be particularly suitable. Thus, a very effective organic solution comprises about 25% of tri-n-octylphosphine oxide in benzene.

The extraction process is broadly applicable to aqueous solutions of diglycolic acid and glycolic acid. The concentration of the acids in water can vary widely. In general, a sufficient amount of water to form a two-phase extraction system is required. From about 1% to about 70%, preferably 5% to 50%, by weight of acids in the aqueous mixture, is suitable. Good results have been obtained using a 20 weight percent solution of acids containing equal parts by weight of diglycolic acid and glycolic acid. However, the relative concentration of diglycolic acid may be substantially less than that of the glycolic acid, and vice versa.

The extraction is carried out by contacting the aqueous mixture of acids with the organic extractant comprising trihycrocarbylphosphine oxide and a solvent, thereby extracting substantially all of the diglycolic acid. Thereafter, the system is allowed to stratify, forming two phases, and the phases are separated. The aqueous phase containing glycolic acid is recovered, and may be distilled to recover the acid. The organic phase is back extracted with water to remove diglycolic acid and recover the extractant, which is recycled. The extraction may be effected at elevated temperature or pressure, depending upon the boiling point of the extractant. However, in most cases, normal temperature and pressure are satisfactory, since the acids decompose at fairly low temperatures.

Preferably the process is carried out continuously. For example, the organic extractant may be passed through a vertical contact vessel in an upward flow countercurrent to a stream of the aqueous acids. More efficient contact of the phases may be obtained by injecting the organic extractant under pressure or by stirring or other physical means. By such methods, small globules of the extractant rise through the aqueous mixture, extracting more and more diglycolic acid as they ascend. The phases are separated by physical treatment such as decanting withdrawing the bottom aqueous layer, etc. In some cases, the phase separation can be combined with the extractant and acids recovery.

The following examples further illustrate the invention. Various modifications of the invention will be apparent from these examples, and accordingly they are not intended to limit the scope of the claims which follow.

EXAMPLES

In the following examples, a 20 weight percent aqueous solution of equal parts diglycolic acid and glycolic acid was extracted using a 23 weight percent solution of tri-n-octylphosphine oxide in benzene.

In each case, the extractant solution was contacted with the aqueous acids mixture by adding the extractant to the mixture with stirring for about 10 minutes. As the system stratified, a two-phase system formed. The lower aqueous layer comprising glycolic acid was withdrawn and the two separated layers were evaporated, esterified with excess methanol, and analyzed in a gas chromatogram as methyl esters of I and II using 2-ethoxyethanol as an internal standard. The results are shown in the following table, where I is glycolic acid and II is diglycolic acid.

|  | Example No. | |
|---|---|---|
|  | 1 | 2 |
| Acid Mix, Parts | | |
| I | 1 | 0.5 |
| II | 1 | 0.5 |
| H$_2$O | 10 | 10 |
| Extractant Parts | 10 | 20 |
| Aqueous Layer, Parts | | |
| I | 0.91 | 0.344 |
| II | 0.09 | 0.149 |
| Benzene Layer, Parts | | |
| I | 0.2 | 0.151 |
| II | 0.77 | 0.289 |
| Beta | 39 | 4.4 |

Beta values were calculated using the following formula: $\beta_{BA} = \text{Wt.I(aq.)/Wt.I(benz)} \div \text{Wt.II(ag.)/Wt.II(benz.)}$

What is claimed is:

1. A process for separating an aqueous solution of glycolic acid and diglycolic acid into component parts which comprises: (1) contacting the solution with an extractant comprising a trihydrocarbylphosphine oxide and a water insoluble organic liquid solvent, to form an organic phase rich in diglycolic acid and an aqueous phase rich in glycolic acid, and (2) separating the phases formed in step (1).

2. A process according to claim 1 wherein the trihydrocarbylphosphine oxide is tri-n-alkylphosphine oxide.

3. A process according to claim 2 wherein the trialkylphosphine oxide contains alkyl groups of from about 1 to about 30 carbon atoms provided that the total number of carbon atoms in the trialkylphosphine oxide is at least 12.

4. A process according to claim 3 wherein the trialkylphosphine oxide is tri-n-octylphosphine oxide.

5. A process according to claim 1 wherein the organic solution comprises from about 5% to about 90%, by weight, of the trihydrocarbylphosphine oxide.

6. A process according to claim 5 wherein the organic solution comprises from about 20% to about 70%, by weight, of the trihydrocarbylphosphine oxide in benzene.

7. A process according to claim 1 wherein the aqueous solution being separated comprises from about 1% to about 70% by weight acids.

8. A process according to claim 7 wherein the aqueous solution being separated comprises from about 5% to about 50% by weight of acids.

9. A process according to claim 5 wherein the acids are present in about equal parts by weight.

10. A process for separating an aqueous mixture comprising about 20% by weight of equal parts of glycolic acid and diglycolic acid acid which comprises: (1) contacting the aqueous mixture with an organic solution of about 25%, by weight, of tri-n-octylphosphine oxide in benzene to form an aqueous phase rich in glycolic acid and an organic phase rich in diglycolic acid; and (2) separating the phases formed in step (1).

* * * * *